United States Patent [19]

Bank

[11] Patent Number: 5,374,756
[45] Date of Patent: Dec. 20, 1994

[54] β-CYANOALKYLSILANE PREPARATION USING AMINO ION EXCHANGE RESIN AS CATALYST

[75] Inventor: Howard M. Bank, Freeland, Mich.

[73] Assignee: Dow Corning Corporation, Midland, Mich.

[21] Appl. No.: 155,895

[22] Filed: Nov. 23, 1993

[51] Int. Cl.$^5$ ............................................. C07F 7/10
[52] U.S. Cl. .................................................... 556/415
[58] Field of Search ......................................... 556/415

[56] References Cited

U.S. PATENT DOCUMENTS

| | | | |
|---|---|---|---|
| 2,823,218 | 2/1958 | Speier et al. | 556/415 X |
| 2,906,764 | 9/1959 | Jex et al. | 556/415 |
| 2,971,970 | 2/1961 | Bluestein | 556/415 |
| 2,971,972 | 2/1961 | Bluestein | 556/415 |
| 4,113,845 | 9/1978 | Litteral | 556/415 |
| 5,126,468 | 6/1992 | Bank | 556/415 |
| 5,126,469 | 6/1992 | Bank | 556/415 |
| 5,247,109 | 9/1993 | Bank | 556/415 |
| 5,262,554 | 11/1993 | Bank | 556/415 |

OTHER PUBLICATIONS

Pike et al., J. Org. Chem. 24, 1939–42, 1959.
Pike et al., J. Org. Chem. 27, 2190–92, 1962.
Rajkumar et al., Organometallics 8, 549–550, 1989.
Belyakova et al., Zhurnal. Obshchei. Khimii 35:1183–1186, 1965.
Kirk-Othmer, Encyclopedia of Chemical Technology, vol. 13, p. 689, 1981, John Wiley and Sons, Inc.

*Primary Examiner*—Paul F. Shaver
*Attorney, Agent, or Firm*—William F. Boley

[57] ABSTRACT

A process for the preparation of hydrolyzable beta-cyanoalkylsilanes. More particularly, this invention relates to the catalytic addition of silicon hydrides to alpha,beta-unsaturated olefinic nitriles to form beta-cyanoalkylsilanes. The present invention employs tertiary and quaternary amino ion exchange resins as a catalyst.

16 Claims, No Drawings

β-CYANOALKYLSILANE PREPARATION USING AMINO ION EXCHANGE RESIN AS CATALYST

BACKGROUND OF INVENTION

The present invention is a process for the preparation of hydrolyzable beta-cyanoalkylsilanes. More particularly, this invention relates to the catalytic addition of silicon hydrides to α,β-unsaturated olefinic nitriles to form β-cyanoalkylsilanes. The present invention employs tertiary and quaternary amino ion exchange resins as a catalyst.

Hydrolyzable beta-cyanoalkylsilanes are useful for the production of polyorganosiloxanes containing the beta-cyanoalkyl substituent. The silicon-bonded beta-cyanoalkyl radical is extremely resistant to hydrolysis and cleavage under hot, humid conditions. Therefore, beta-cyanoalkylsilanes find particular use in the preparation of polyorganosiloxanes which must be subjected to hot, humid conditions. The presence of the silicon-bonded beta-cyanoalkyl radical substituted on polyorganosiloxanes also tends to stabilize the polyorganosiloxanes against swelling induced by liquid hydrocarbons.

Jex et al., U.S. Pat. No. 2,906,764, issued Sep. 29, 1959, describe a process for producing cyanoalkylsilanes by reacting an olefinic nitrile with a silane, the silane having at least one hydrogen and one hydrolyzable group bonded to the silicon atom, in the presence of a diarylamine catalyst.

Pike et al., J. Org. Chem. 24, 1939–42, 1959, describe tertiary amines as effective directive catalysts for the reaction of trichlorosilane with acrylonitrile to form beta-cyanoethyltrichlorosilane.

Pike et al., J. Org. Chem. 27, 2190–92, 1962, describe preparation of beta-cyanoethyltrichlorosilane by reacting trichlorosilane with acrylonitrile in the presence of silylamine catalysts of the general formula $(CH_3)_3SiNR_2$, where the nitrogen atom of the silylamine is attached to the silicon atom.

Bluestein, U.S. Pat. No. 2,971,970, issued Feb. 14, 1961, describes a process for reacting hydrolyzable silicon hydride with an α,β-unsaturated olefinic nitrile to form a cyanoalkylsilane where the catalyst comprises (A) a cuprous compound, (B) a diamine, and (C) a trialkylamine.

Bluestein, U.S. Pat. No. 2,971,972, issued Feb. 14, 1961, describes a process for reacting phenyldichlorosilane and acrylonitrile to form β-cyanoethylphenyldichlorosilane without the necessity for employing a diamine. The process is conducted in the presence of a cuprous compound selected from a group consisting of cuprous oxide and cuprous halides, and in the presence of a trialkylamine.

Rajkumar et al., Organometallics 8, 549–550, 1989, describe a catalyst system consisting of tetramethylethylenediamine and cuprous oxide for the hydrosilylation of acrylonitrile to give the β-adduct.

Bank, U.S. Pat. No. 5,126,468, issued Jun. 30, 1992, describes a process for the preparation of hydrolyzable β-cyanoalkylsilanes by the catalytic addition of hydrolyzable silicon hydrides to α,β-unsaturated olefinic nitriles. The process employs a catalyst comprising a diamine and nonactivated copper or a compound of copper selected from a group consisting of copper metal, Cu(II) halide, Cu(II) oxide, copper sulfate, copper sulfide, and copper cyanide compounds, Cu(I) thiocyanide, and copper chromium compounds.

Bank, U.S. Pat. No. 5,126,469, issued Jun. 30, 1992, describes a process for the preparation of hydrolyzable β-cyanoalkylsilanes by the catalytic addition of hydrolyzable silicon hydrides to α,β-unsaturated olefinic nitriles using a supported catalyst. The supported catalyst comprises a diamine and supported copper or a support copper compound.

Belyakova et al., Zhurnal. Obshchei. Khimii 35:1183–1186, 1965, describe the reaction of trichlorosilane with acrylonitrile in the presence of a secondary amino ion exchange resin at a temperature of 110° C. to 120° C.

SUMMARY OF INVENTION

A process for the preparation of hydrolyzable beta-cyanoalkylsilanes. More particularly, this invention relates to the catalytic addition of silicon hydrides to α,β-unsaturated olefinic nitriles to form β-cyanoalkylsilanes. The present invention employs tertiary and quaternary amino ion exchange resins as a catalyst. The process is conducted at a temperature within a range of about 100° C. to 250° C.

DESCRIPTION OF INVENTION

The present invention is a process for preparation of beta-cyanoalkylsilanes described by formula:

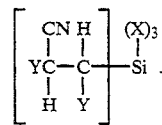 (1)

The process comprises contacting a silicon hydride described by formula

 (2)

with an unsaturated olefinic nitrile described by formula

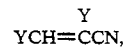 (3)

in the presence of a catalyst selected from a group consisting of tertiary amino ion exchange resins and quaternary amino ion exchange resins at a temperature within a range of about 100° C. to 250° C.; where X is a halogen and each Y is independently selected from a group consisting of hydrogen and lower alkyl radicals comprising one to eight carbon atoms.

The described process is applicable to the production of beta-cyanoalkylsilanes containing one silicon-bonded beta-cyanoalkyl radical, as described by Formula 1. Beta-cyanoalkylsilanes that can be made by the present process are, for example, beta-cyanoethyltrichlorosilane, beta-cyanopropyltrichlorosilane, beta-cyanobutyltrichlorosilane, beta-cyanopentyltrichlorosilane, beta-cyanopentyltrichlorosilane, beta-cyanopropyltrichlorosilane, beta-cyanohexyltrichlorosilane, beta-cyanoheptyltrichlorosilane, beta-cyanooctyltrichlorosilane, alpha-methyl-beta-cyanoethyltrichlorosilane, alpha-ethyl-beta-cyanoethyltrichlorosilane, alpha-octyl-beta-cyanopropyltrichlorosilane, beta-cyanoethyltribromosilane, and beta-cyanopropyltrifluorosilane. The preferred beta-cyanoalkylsilane made by the present process is beta-cyanoethyltrichlorosilane.

The silicon hydride, described by Formula 2, contains one silicon-bonded hydrogen atom and three silicon-bonded halogen atoms. The halogen atom, X, can be selected from a group consisting of bromine, chlorine, fluorine, and iodine. The preferred halogen is chlorine.

The silicon hydride is contacted with an $\alpha,\beta$-unsaturated olefinic nitrile described by Formula 3. The $\alpha,\beta$-unsaturated olefinic nitrile contains substituents Y which are independently selected from a group consisting of hydrogen and lower alkyl radicals comprising from one to eight carbon atoms. For example, Y can be methyl, ethyl, propyl, butyl, tert-butyl, pentyl, hexyl, heptyl, and octyl. Examples of the $\alpha,\beta$-unsaturated olefinic nitrile include acrylonitrile, methacrylonitrile, crotononitrile, ethylacrylonitrile, 1- cyanobutene-1, and 2-cyanooctene-1. The preferred $\alpha,\beta$-unsaturated olefinic nitrile is acrylonitrile.

The molar ratio of the silicon hydride to the $\alpha,\beta$-unsaturated olefinic nitrile may be varied within wide limits, however no particular advantage is derived from employing a molar excess of either reactant. The use of molar excesses of either of the two reactants is not precluded. It is preferred that the molar ratio of silicon hydride to $\alpha,\beta$-unsaturated olefinic nitrile be within a range of about 0.5 to 1.5. In the most preferred embodiment of the invention, the molar ratio of silicon hydride to $\alpha,\beta$-unsaturated olefinic nitrile is about 1.0.

The silicon hydride and $\alpha,\beta$-unsaturated olefinic nitrile are contacted in the presence of a catalyst selected from a group consisting of tertiary amino ion exchange resin and quaternary amino ion exchange resin. General methods for making such catalyst are discussed in, for example, Litteral, U.S. Pat. No. 4,113,845, issued Sep. 12, 1978, which is incorporated herein by reference.

The tertiary and quaternary amino ion exchange resins useful in the present invention are polymeric materials which are insoluble in trichlorosilane, the $\alpha,\beta$-unsaturated olefinic nitriles, and the products of the present process. Such insolubility can be achieved, in the case of linear, thermoplastic ion exchange resins by using resin of sufficiently high molecular weight, i.e. greater than about 10,000, such that the polymers possess the requisite insolubility. Insolubility can be achieved by employing a cross-linked ion exchange resin, which may be infusible as well. However for purposes of this invention the degree of cross-linking need only be sufficient to meet the requisite insolubility requirements.

The amino functionality in the resin is a tertiary amino or quaternary amino group attached through carbon to the resin structure. Except for the nitrogen atoms or the halide ions of the amino functionality all of the resin is composed of carbon and hydrogen.

The ion exchange resins use in the present invention are those made from the copolymerization of monoolefinically unsaturated hydrocarbons and a polyolefinically unsaturated hydrocarbons. The monoolefinically unsaturated compounds can be, for example, styrene, 4-chlorostyrene, 3-chlorostyrene, vinyltoluene, and 4-chloromethylstyrene. The polyolefinically unsaturated compounds may be, for example, 1,4-divinylbenzene, divinyltoluenes, and trivinylbenzene.

Such copolymers are well known and a number of them are commercial products which possess tertiary amino or quaternary amino functionality. They may be converted into cross-linked resins with conventional free radical addition catalysts such as peroxides. The chloro groups of the copolymer can be replaced by a condensation reaction with a secondary or tertiary alkylamine, arylamine, or alkylarylamine; where each alkyl comprises one to 20 carbon atoms and each aryl comprises six to twelve carbon atoms. The tertiary amino ion exchange resin is formed by reacting the chloro groups of the copolymer with a secondary amine. The quaternary amino ion exchange resin is formed by reacting the chloro groups of the copolymer with a tertiary amine. Quaternization of the tertiary amine containing resin can be effected, for example, by reaction with a hydrocarbon halide such as an alkyl halide or aryl halide, to form the corresponding quaternary amine halide.

It is preferred that the amino ion exchange resin be of the macroreticular type as described, for example, in Kirk-Othmer, Encyclopedia of Chemical Technology, Vol. 13, p. 689, 1981, John Wiley and Sons, Inc.

A preferred amino ion exchange resin for use in the present process is a cross-linked styrene/divinylbenzene copolymer resin having tertiary amino ion functionality or quaternary amino functionality. More preferred is when the tertiary amino ion functionality is dimethylamino and the quaternary amino functionality is trimethylamino chloride. Examples of amino ion exchange resins useful in the present invention are typified by Amberlyst A-21, Amberlyst A-26, Amberlyst A-27, and Amberlyst A-29, Rohm and Haas Company, Philadelphia, Pa.

The amount of catalyst employed in the present process in relation to the amount of $\alpha,\beta$-unsaturated olefinic nitrile may be varied within wide limits and is dependent upon such conditions as the temperature at which the process is run, the surface area of the catalyst, and whether the process is run as a batch or continuous process. In general, the process can be run under conditions where the catalyst is present at about 0.1 to 50 weight percent of a mixture comprising the catalyst, the $\alpha,\beta$-unsaturated olefinic nitrile, and the silicon hydride. Preferred is when the catalyst comprises about 0.5 to 30 weight percent of the mixture.

The silicon hydride, the $\alpha,\beta$-unsaturated olefinic nitrile and the catalyst are contacted in a suitable reactor of standard design. The type of reactor is not critical.

The process can be run as a batch process, a semi-batch process, or a continuous process. A preferred process is where the reaction is conducted as a continuous process in a packed-bed reactor.

The temperature for conducting the process can be within a range of about 100° C. to 250° C. It is preferred that the temperature be within a range greater than 120° C. to about 200° C. Generally, higher temperatures allow the use of a lower catalyst concentration.

The pressure under which the process is conducted is not critical. Generally, the process can be run at a pressure within a range of about 0 psig to 1000 psig. Preferred is a pressure within a range of about 0 psig to 100 psig.

The time required for conducting the process may vary depending on the particular silicon hydride, $\alpha,\beta$-unsaturated olefinic nitrile, temperature, and catalyst concentration employed. In general, reaction times of 0.1 to 30.0 hours are useful. A preferred reaction time is about 0.5 to 20.0 hours.

The following example is given to illustrate the present invention. This example is not intended to limit the present claims.

EXAMPLE 1

The ability of a styrene/divinylbenzene copolymer based resin containing tertiary amino functionality to catalyze the addition of trichlorosilane to acrylonitrile to form β-cyanoethyltrichlorosilane was evaluated in a series of runs.

The runs were conducted in sealed glass tubes purged with argon. The runs were conducted by placing the weight of dry catalyst given in Table 1 into a tube, then adding to each tube 2 mL of a mixture of 0.0124 mole of trichlorosilane and 0.0113 mole of acrylonitrile. The tubes were sealed and then heated for 2 hours at either 120° C. or 170° C. The catalyst tested consisted of Amberlyst A-21, Rohm and Haas Company, Philadelphia, Pa. Amberlyst A-21 is described as a styrene/divinylbenzene copolymer Amberlyst A-21 is described as a styrene/divinylbenzene copolymer based resin having dimethyl tertiary amino functionality and an effective size of 0.40 mm to 0.55 mm.

The results of these runs are presented in Table 1. The contents of individual tubes were analyzed by gas liquid chromatography(GLC) using a thermal conductivity detector(TCD). The results are expressed as the area percent(Area %) under the GLC-TCD trace for beta-cyanoethyltrichlorosilane, as a percentage of the total area under the GLC-TCD trace.

TABLE 1

Amberlyst A-21 Catalyzed
Reaction of Trichlorosilane with Acrylonitrile

| Run No. | Catalyst Weight (g) | Temperature °C. | Area % β-Cyanoethyltrichlorosilane |
|---|---|---|---|
| 1 | 0.0142 | 120 | 2.0 |
| 2 | 0.0184 | 170 | 80.0 |

EXAMPLE 2

The ability of a styrene/divinylbenzene copolymer based resin containing quaternary amino functionality to catalyze the addition of trichlorosilane to acrylonitrile to form β-cyanoethyltrichlorosilane was evaluated in a series of runs.

The runs were conducted in sealed glass tubes purged with argon. The runs were conducted by placing the weight of dry catalyst given in Table 2 into a tube, then adding to each tube 2 mL of a mixture of 0.0124 mole of trichlorosilane and 0.0113 mole of acrylonitrile. The tubes were sealed and heated for 2 hours at either 120° C. or 170° C. The catalyst tested consisted of Amberlyst A-27, Rohm and Haas Company, Philadelphia, Pa. Amberlyst A-27 is described as a styrenedivinylbenzene copolymer based resin having trimethyl tertiary amino functionality, with chloride as the cation, and an effective size of 0.40 mm to 0.50 mm.

The results of these runs are presented in Table 2. The contents of individual tubes were analyzed by GLC-TCD. The results are expressed as the area percent-(Area %) under the GLC-TCD trace for beta-cyanoethyltrichlorosilane, as a percentage of the total area under the GLC-TCD trace.

TABLE 2

Amberlyst A-27 Catalyzed
Reaction of Trichlorosilane with Acrylonitrile

| Run No. | Catalyst Weight | Temperature °C. | Area % β-Cyanoethyltrichlorosilane |
|---|---|---|---|
| 1 | 0.0316 | 120 | 7.1 |
| 2 | 0.0366 | 170 | 75.7 |

I claim:

1. A process for preparation of beta-cyanoalkylsilanes described by formula

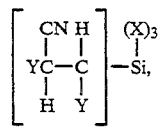

the process comprising:
contacting a silicon hydride described by formula

with an unsaturated olefinic nitrile described by formula

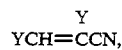

in the presence of a catalyst selected from a group consisting of tertiary amino ion exchange resins and quaternary amino ion exchange resins at a temperature within a range of about 100° C. to 250° C.; where X is a halogen and each Y is independently selected from a group consisting of hydrogen and lower alkyl radicals comprising one to eight carbon atoms.

2. A process according to claim 1, where the temperature is within a range of greater than 120° C. to about 200° C.

3. A process according to claim 1, where the halogen is chlorine.

4. A process according to claim 1, where the silicon hydride is trichlorosilane.

5. A process according to claim 1, where the unsaturated olefinic nitrile is selected from a group consisting of acrylonitrile, methacrylonitrile, crotononitrile, ethylacrylonitrile, 1-cyanobutene-1, and 2-cyanooctene-1.

6. A process according to claim 1, where the unsaturated olefinic nitrile is acrylonitrile.

7. A process according to claim 1, where the beta-cyanoalkylsilane is beta-cyanoethyltrichlorosilane.

8. A process according to claim 1, where the silicon hydride is trichlorosilane, the olefinic nitrile is acrylonitrile and the temperature is within a range of greater than 120° C. to about 200° C.

9. A process according to claim 1, where the mole ratio of silicon hydride to unsaturated olefinic nitrile is about 1.0.

10. A process according to claim 1, where the process is conducted for a time period in a range of about 0.1 to 30 hours.

11. A process according to claim 1, where the catalyst is a cross-linked styrene/divinylbenzene copolymer resin having tertiary amino functionality formed by attachment of a dialkylamino group through a carbon atom to the resin.

12. A process according to claim 11, where the dialkylamino group is dimethylamino.

13. A process according to claim 1, where the catalyst is a cross-linked styrene/divinylbenzene copolymer resin having a quaternary amino functionality formed by attachment of a trialkylamino group through carbon to the resin.

14. A process according to claim 13, where the trialkylamino group is trimethylamino.

15. A process according to claim, 11 where the resin is of the macroreticular type.

16. A process according to claim 13, where the resin is of the macroreticular type.

* * * * *